US010179097B2

(12) United States Patent
Nicou et al.

(10) Patent No.: US 10,179,097 B2
(45) Date of Patent: *Jan. 15, 2019

(54) DYE COMPOSITION COMPRISING A PARA-PHENYLENEDIAMINE OXIDATION BASE AND AN AMPHOTERIC OR CATIONIC POLYMER IN A MEDIUM RICH IN FATTY SUBSTANCES

(71) Applicant: L'OREAL, Paris (FR)

(72) Inventors: Valérie Nicou, Clichy (FR); Isabelle Rollat, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/536,998

(22) PCT Filed: Dec. 11, 2015

(86) PCT No.: PCT/EP2015/079432
§ 371 (c)(1),
(2) Date: Jun. 16, 2017

(87) PCT Pub. No.: WO2016/096654
PCT Pub. Date: Jun. 23, 2016

(65) Prior Publication Data
US 2017/0354579 A1 Dec. 14, 2017

(30) Foreign Application Priority Data

Dec. 17, 2014 (FR) ...................................... 14 62620

(51) Int. Cl.
A61Q 5/10 (2006.01)
A61K 8/41 (2006.01)
A61K 8/31 (2006.01)
A61K 8/73 (2006.01)
A61K 8/81 (2006.01)
A61K 8/84 (2006.01)

(52) U.S. Cl.
CPC ................ A61K 8/411 (2013.01); A61K 8/31 (2013.01); A61K 8/731 (2013.01); A61K 8/817 (2013.01); A61K 8/8158 (2013.01); A61K 8/84 (2013.01); A61Q 5/10 (2013.01)

(58) Field of Classification Search
CPC ........ A61Q 5/10; A61K 8/731; A61K 8/8158; A61K 8/22; A61K 8/817; A61K 2800/882
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 3,206,462 A | 9/1965 | McCarty |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,075,136 A | 2/1978 | Schaper |
| 4,131,576 A | 12/1978 | Iovine et al. |
| 4,165,367 A | 8/1979 | Chakrabarti |

(Continued)

FOREIGN PATENT DOCUMENTS

| DE | 2359399 A1 | 6/1975 |
| DE | 3843892 A1 | 6/1990 |

(Continued)

OTHER PUBLICATIONS

Non-Final Office Action for copending U.S. Appl. No. 15/537,016, dated Jul. 10, 2018.
Non-Final Office Action for copending U.S. Appl. No. 15/537,225, dated Jul. 10, 2018.
Final Office Action for copending U.S. Appl. No. 15/537,041, dated May 18, 2018.
Notice of Allowance for copending U.S. Appl. No. 15/537,029, dated Aug. 1, 2018.
Final Office Action for copending U.S. Appl. No. 15/537,060, dated May 1, 2018.

(Continued)

Primary Examiner — Eisa B Elhilo
(74) Attorney, Agent, or Firm — The Marbury Laqw Group, PLLC

(57) ABSTRACT

The present invention relates to a composition for dyeing keratin fibers, in particular keratin fibers such as the hair, comprising: a) at least one oxidation base 3-(2,5-diaminophenyl)-1-propanol and/or acid salts thereof and/or solvates thereof such as hydrates; b) at least one coupler; c) at least one polymer chosen from cationic polymers and amphoteric polymers, and mixtures thereof; d) at least one fatty substance; the total amount of fatty substances being at least 10%, e) optionally at least one basifying agent; and f) optionally at least one chemical oxidizing agent. The invention also relates to a process for dyeing keratin fibers such as the hair using the composition of the invention, and to a multi-compartment device for using the composition of the invention.

19 Claims, No Drawings

(56) References Cited

U.S. PATENT DOCUMENTS

| | | | |
|---|---|---|---|
| 4,166,894 A | 9/1979 | Schaper | |
| RE30,199 E | 1/1980 | Rose et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,608,250 A | 8/1986 | Jacquet et al. | |
| 4,719,099 A | 1/1988 | Grollier et al. | |
| 4,839,166 A | 6/1989 | Grollier et al. | |
| 4,840,639 A | 6/1989 | Husemeyer et al. | |
| 4,996,059 A | 2/1991 | Grollier et al. | |
| 5,009,880 A | 4/1991 | Grollier et al. | |
| 5,061,289 A | 10/1991 | Clausen et al. | |
| 5,089,252 A | 2/1992 | Grollier et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,616,150 A | 4/1997 | Moeller et al. | |
| 5,663,366 A | 9/1997 | Neunhoeffer et al. | |
| 5,766,576 A | 6/1998 | Lowe et al. | |
| 5,928,385 A | 7/1999 | Cotteret et al. | |
| 5,958,392 A | 9/1999 | Grollier et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,342,079 B1 | 1/2002 | Pan et al. | |
| 6,503,282 B1* | 1/2003 | Braun | A61K 8/411 564/443 |
| 6,645,258 B2 | 11/2003 | Vidal et al. | |
| 6,730,789 B1 | 5/2004 | Birault et al. | |
| 3,066,781 A1 | 11/2011 | Hercouet et al. | |
| 2002/0010970 A1* | 1/2002 | Cottard | A61K 8/342 8/405 |
| 2002/0046431 A1 | 4/2002 | Laurent et al. | |
| 2010/0154136 A1 | 6/2010 | Hercouet et al. | |
| 2011/0158925 A1 | 6/2011 | Ascione et al. | |
| 2013/0048007 A1 | 2/2013 | Fadli | |
| 2014/0137342 A1 | 5/2014 | Guerin et al. | |
| 2014/0318566 A1 | 10/2014 | Mignon et al. | |
| 2015/0082554 A1 | 3/2015 | Allard et al. | |
| 2015/0202142 A1 | 7/2015 | Charrier et al. | |
| 2015/0335563 A1 | 11/2015 | Allard et al. | |

FOREIGN PATENT DOCUMENTS

| | | |
|---|---|---|
| DE | 4133957 A1 | 4/1993 |
| DE | 19543988 A1 | 5/1997 |
| EP | 0007537 A1 | 2/1980 |
| EP | 0080976 A1 | 6/1983 |
| EP | 0122324 A1 | 10/1984 |
| EP | 0337354 A1 | 10/1989 |
| EP | 0770375 A1 | 5/1997 |
| EP | 1166749 A2 | 1/2002 |
| EP | 2198929 A1 | 6/2010 |
| EP | 2338463 A1 | 6/2011 |
| FR | 1400366 A | 5/1965 |
| FR | 2077143 A5 | 10/1971 |
| FR | 2080759 A1 | 11/1971 |
| FR | 2190406 A2 | 2/1974 |
| FR | 2270846 A1 | 12/1975 |
| FR | 2316271 A1 | 1/1977 |
| FR | 2320330 A1 | 3/1977 |
| FR | 2336434 A1 | 7/1977 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2519863 A1 | 7/1983 |
| FR | 2598611 A1 | 11/1987 |
| FR | 2733749 A1 | 11/1996 |
| FR | 2801308 A1 | 5/2001 |
| FR | 2886136 A1 | 12/2006 |
| FR | 2988591 A1 | 10/2013 |
| FR | 2988594 A1 | 10/2013 |
| FR | 2988595 A1 | 10/2013 |
| FR | 2988598 A1 | 10/2013 |
| FR | 2994085 A1 | 2/2014 |
| GB | 1021400 A | 3/1966 |
| GB | 1026978 A | 4/1966 |
| GB | 1153196 A | 5/1969 |
| GB | 1546809 A | 5/1979 |
| JP | 02-019576 A | 1/1990 |
| JP | 05-163124 A | 6/1993 |
| WO | 80/00214 A1 | 2/1980 |
| WO | 94/08969 A1 | 4/1994 |
| WO | 94/08970 A1 | 4/1994 |
| WO | 94/24988 A1 | 11/1994 |
| WO | 96/15765 A1 | 5/1996 |
| WO | 01/51019 A1 | 7/2001 |
| WO | 2012/080288 A1 | 6/2012 |
| WO | 2012/080289 A2 | 6/2012 |
| WO | 2012/080321 A2 | 6/2012 |
| WO | 2013/144260 A2 | 10/2013 |
| WO | 2013/152956 A2 | 10/2013 |
| WO | 2014/020148 A1 | 2/2014 |
| WO | 2016/096655 A1 | 6/2016 |
| WO | 2016/097022 A1 | 6/2016 |
| WO | 2016/097226 A1 | 6/2016 |
| WO | 2016/097227 A1 | 6/2016 |
| WO | 2016/097228 A1 | 6/2016 |
| WO | 2016/097229 A1 | 6/2016 |

OTHER PUBLICATIONS

Final Office Action for copending U.S. Appl. No. 15/537,029, dated Apr. 17, 2018.
International Search Report for PCT/EP2015/079434, dated Feb. 1, 2016.
International Search Report for PCT/EP2015/080051, dated Mar. 9, 2016.
International Search Report for PCT/EP2015/079432, dated Mar. 16, 2016.
International Search Report for PCT/EP2015/080370, dated Mar. 14, 2016.
International Search Report for PCT/EP2015/080371, dated Mar. 24, 2016.
International Search Report for PCT/EP2015/080372, dated May 3, 2016.
International Search Report for PCT/EP2015/080373, dated Feb. 9, 2016.
Non-Final Office Action for co-pending U.S. Appl. No. 15/537,029, dated Oct. 2, 2017.
Non-Final Office Action for co-pending U.S. Appl. No. 15/537,041, dated Oct. 2, 2017.
Non-Final Office Action for co-pending U.S. Appl. No. 15/537,060, dated Sep. 29, 2017.

* cited by examiner

DYE COMPOSITION COMPRISING A PARA-PHENYLENEDIAMINE OXIDATION BASE AND AN AMPHOTERIC OR CATIONIC POLYMER IN A MEDIUM RICH IN FATTY SUBSTANCES

CROSS REFERENCE TO RELATED APPLICATIONS

This is a national stage application of PCT/EP2015/079432, filed internationally on Dec. 11, 2015, which claims priority to French Application No. 1462620, filed on Dec. 17, 2014, both of which are incorporated by reference herein in their entireties.

The present invention relates to a composition for dyeing keratin fibres using a specific para-phenylenediamine oxidation base, an amphoteric or cationic polymer and at least 10% of fatty substances.

Many people have sought for a long time to modify the colour of their hair and in particular to mask their grey hair.

One of the dyeing methods is "permanent" or oxidation dyeing, which uses dye compositions containing oxidation dye precursors, generally known as oxidation bases. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouring modifiers, the latter being chosen especially from aromatic meta-diamines, meta-aminophenols, meta-diphenols and certain heterocyclic compounds such as indole compounds. The variety of the molecules used as oxidation bases and couplers allows a wide range of colours to be obtained.

Permanent dyeing processes thus consist in using, with the composition containing the dye precursors, an aqueous composition comprising at least one oxidizing agent, under alkaline pH conditions in the vast majority of cases. The role of this oxidizing agent is to at least partly degrade the melanin of the hair, which, depending on the nature of the oxidizing agent present, leads to more or less pronounced lightening of the fibres. The oxidizing agent used is generally hydrogen peroxide.

The basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

In the long term, the use of an oxidizing agent and an alkaline agent may lead to degradation of the keratin fibres and also to inconvenience at the time of use; in particular, ammonia may give rise to inconvenience to the user due to its strong characteristic odour.

Moreover, not only may the user be inconvenienced by the odour, but he may also be confronted with greater risks of intolerance, for instance irritation of the scalp, which is especially reflected by stinging.

It is also important to obtain intense colouring, which is resistant to external factors such as light, shampoos and sweat, and which is as uniform as possible along the entire fibre, irrespective of the level of damage of the keratin fibre.

Oxidation bases of the para-phenylenediamine type are commonly used in the field of hair dyeing. It is known practice, for example, to use 3-(2,5-diaminophenyl)-1-propanol (or 2-γ-hydroxypropyl-para-phenylenediamine) in oxidation dyeing, especially in document WO 80/00214. However, the dye compositions obtained using this oxidation base are not always satisfactory especially for ensuring suitable coverage of grey hair with an acceptable colouring selectivity between the root and the end and/or sufficient fastness with respect to external attacking factors such as light, shampoos, bad weather, etc.

One of the objects of the present invention is to propose compositions for dyeing human keratin fibres such as the hair, which have superior dyeing properties relative to the existing compositions.

In particular, the composition according to the invention in the presence of a chemical oxidizing agent must make it possible to obtain colours that are satisfactory, especially in terms of power, but also with sufficient uniformity of the colour from the end to the root of the hair, which makes it possible to avoid a "root" effect of the colouring. Finally, it is also possible to obtain colourings that are very stable towards external agents.

Furthermore, the invention makes it possible to achieve substantial degrees of lightening while at the same time colouring, and does so without using oxidizing agents such as persalts or increasing the amount of chemical oxidizing agent or of basifying agent.

Moreover, the composition of the invention makes it possible to obtain formulations that are less malodorous during their application to the hair or during their preparation.

These aims and others are achieved by the present invention, one subject of which is thus a composition for dyeing keratin fibres, in particular human keratin fibres such as the hair, comprising:
 a) at least one oxidation base 3-(2,5-diaminophenyl)-1-propanol and/or acid salts thereof and/or solvates thereof such as hydrates;
 b) at least one coupler;
 c) at least one polymer chosen from cationic polymers and amphoteric polymers, and mixtures thereof;
 d) at least one fatty substance;
 the total amount of fatty substances being at least 10% by weight relative to the total weight of the composition,
 e) optionally at least one basifying agent; and
 f) optionally at least one chemical oxidizing agent.

A subject of the invention is also a process for dyeing keratin fibres such as the hair using the composition of the invention, and a multi-compartment device for using the composition of the invention.

Furthermore, the processes according to the invention use formulations that are less malodorous during their application to the hair or during their preparation.

Other characteristics and advantages of the invention will emerge more clearly on reading the description and the examples that follow.

In the text hereinbelow, and unless otherwise indicated, the limits of a range of values are included within that range. The expression "at least one" is equivalent to the expression "one or more".

a) 3-(2,5-Diaminophenyl)-1-propanol oxidation bases:

The composition of the invention comprises a) one or more oxidation bases chosen from 3-(2,5-diaminophenyl)-1-propanol (or 2-γ-hydroxypropyl-para-phenylenediamine) having the following formula, the acid salts thereof or the solvates thereof such as hydrates:

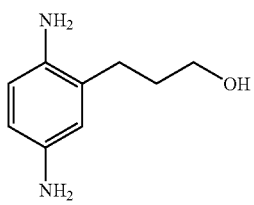 [SMILES: Nc1ccc(N)c(CCCO)c1]

The oxidation base(s) chosen from (2,5-diaminophenyl) propanol, the acid salts thereof or the solvates thereof such as hydrates, according to the invention, may be present in the composition of the invention in an amount ranging from 0.0001% to 20% by weight relative to the total weight of the composition, preferably from 0.005% to 10% by weight and more particularly from 0.01% to 10% by weight relative to the total weight of the composition.

The acid salts that may be used according to the invention may be chosen from hydrochlorides, hydrobromides, sulfates, citrates, succinates, tartrates, lactates, tosylates, benzenesulfonates, phosphates and acetates.

Additional Base

The composition according to the invention may comprise one or more additional oxidation bases other than 3-(2,5-diaminophenyl)-1-propanol, acid salts thereof or solvates thereof such as hydrates. According to a particular embodiment of the invention, the additional base(s) are chosen from heterocyclic bases and benzene-based bases, and addition salts thereof or solvates thereof.

As examples of additional benzene-based oxidation bases, mention may be made of para-phenylenediamines other than 3-(2,5-diaminophenyl)-1-propanol, bis(phenyl)alkylenediamines, para-aminophenols and ortho-aminophenols, and the addition salts or solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)para-phenylenediamine, 4-N,N-bis(β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl) pyrrolidine, and the addition salts thereof with an acid, or the solvates thereof.

Among the para-phenylenediamines mentioned above, para-phenylenediamine or PPD, para-tolylenediamine or PTD, 2-isopropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, or the solvates thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof, or the solvates thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid, or the solvates thereof.

Among the ortho-aminophenols, examples that may be mentioned include 2-aminophenol, 2-amino-5-methylphenol, 2-amino-6-methylphenol, 5-acetamido-2-aminophenol and the addition salts thereof, or the solvates thereof.

The heterocyclic bases are more particularly chosen from pyridine derivatives, pyrimidine derivatives and pyrazole derivatives, and the addition salts thereof, or the solvates thereof.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof, or the solvates thereof.

Other pyridine oxidation bases that are useful in the dyeing process according to the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a] pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl) methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, 2-[(3-aminopyrazolo[1,5-a]pyridin-2-yl)oxy]ethanol, and the addition salts thereof, or the solvates thereof.

Among the pyrimidine derivatives, mention may be made of the compounds described, for example, in patents DE 2359399, JP 88-169571, JP 05-63124 and EP 0/770/375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and the tautomeric forms thereof, when a tautomeric equilibrium exists.

Among the pyrazole derivatives mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt or solvate thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt or solvate thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or 2-(3-aminopyrazolo[1,5-a]pyridin-2-yloxy)ethanol and/or a salt or solvate thereof.

The additional oxidation base(s) according to the invention each advantageously represent from 0.0001% to 10% by weight relative to the total weight of the composition, and preferably from 0.005% to 5% by weight relative to the total weight of the composition.

b) Couplers

The composition of the invention comprises at least one coupler b). Among these couplers, mention may be made especially of meta-phenylenediamines, meta-aminophenols, meta-diphenols, naphthalene-based couplers and heterocyclic couplers, and also the addition salts or solvates thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2,4-diamino-1-(β-hydroxyethyloxy)benzene, 1-methyl-2-hydroxy-4-β-hydroxyethylamino benzene, 2-methyl-5-aminophenol, 5-amino-6-chloro-2-methylphenol, 2-amino-4-(β-hydroxyethylamino)-1-methoxybenzene, 1,3-diaminobenzene, 1,3-bis(2,4-diaminophenoxy)propane, 3-ureidoaniline, 3-ureidol-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy4-methylpyridine, 1-H3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid or the solvates thereof, and mixtures thereof.

The coupler(s) each advantageously represent from 0.0001% to 10% by weight relative to the total weight of the composition and preferably from 0.005% to 5% by weight relative to the total weight of the composition of the invention.

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

Additional Dyes

The composition of the invention may also comprise one or more direct dyes. The latter dyes are more particularly chosen from ionic or nonionic species, preferably cationic or nonionic species. These direct dyes may be synthetic or of natural origin. When theyare present, the direct dye(s) more particularly represent from 0.0001% to 10% by weight and preferably from 0.005% to 5% by weight relative to the total weight of the composition.

c) Cationic and Amphoteric Polymers

The composition of the invention contains at least one polymer chosen from cationic polymers and amphoteric polymers, and mixtures thereof.

In the composition of the invention, the polymer(s) chosen from cationic polymers and amphoteric polymers may represent from 0.01% to 10%, better still from 0.05% to 7% and even more preferentially from 0.1% to 5% by weight relative to the total weight of the composition.

Cationic Polymer

The cationic polymers that may be used in the composition according to the invention are advantageously chosen from cationic polymers with a charge density of greater than or equal to 4 milliequivalents per gram (meq./g).

Preferably, the cationic polymer has a charge density of greater than or equal to 5 milliequivalents per gram (meq./g), preferably ranging from 5 to 20 meq./g and more particularly from 5.5 to 10 meq./g.

The cationic charge density of a polymer corresponds to the number of moles of cationic charges per unit mass of polymer under conditions in which it is totally ionized. It may be determined by calculation if the structure of the polymer is known, i.e. the structure of the monomers constituting the polymer and their molar proportion or weight proportion. It may also be determined experimentally via the Kjeldahl method, generally at a pH of about 7 at room temperature.

The cationic polymers, preferably with a cationic charge density of greater than 4 meq./g, which may be used in accordance with the present invention, may be chosen from any polymer known per se as improving the cosmetic properties of hair treated with compositions, i.e. especially those described in patent application EP-A-0 337 354 and in French patent applications FR-A-2 270 846, 2 383 660, 2 598 611, 2 470 596 and 2 519 863.

In general, for the purposes of the present invention, the term "cationic polymer" denotes any polymer comprising cationic groups and/or groups that may be ionized into cationic groups.

The cationic polymers are chosen from those containing units comprising primary, secondary, tertiary and/or quaternary amine groups that either may form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers, mention may more particularly be made of polymers of the polyamine, polyamino amide and polyquaternary ammonium type.

Among these polymers, mention may be made of the following families:

(1) homopolymers or copolymers derived from acrylic or methacrylic esters or amides and comprising at least one of the units of formulae (I) to (IV) below:

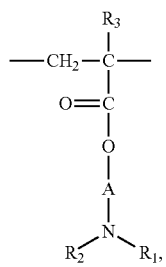

(I)

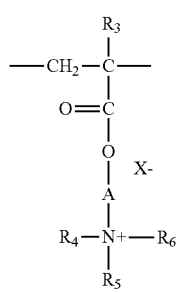

(II)

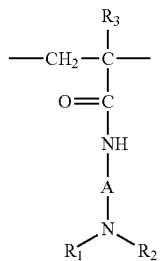

(III)

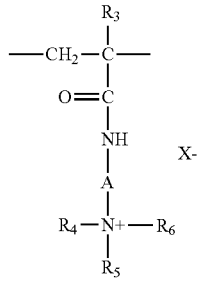

(IV)

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl;

$X^-$ denotes an anion derived from a mineral or organic acid, such as a methosulfate anion or a halide, especially chloride or bromide.

The copolymers of family (1) may also comprise one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulfate or with a dimethyl halide, the copolymers of acrylamide and of methacryloyloxyethyltrimethylammonium chloride described, for example, in patent application EP-A-080 976, the copolymers of acrylamide and of methacryloyloxyethyltrimethylammonium methosulfate, quaternized or non-quaternized vinylpyrrolidone/dialkylaminoalkyl acrylate or methacrylate copolymers. These polymers are described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, quaternized vinylpyrrolidone/dimethylaminopropylmeth-
acrylamide copolymers, and crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba, and mixtures thereof.

(2) cyclopolymers of alkyldiallylamine or of dialkyldiallylammonium, such as the homopolymers or copolymers comprising, as constituent of the chain, units corresponding to formula (V) or (VI):

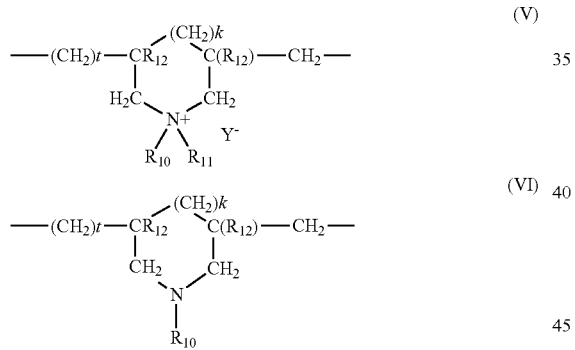

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group containing from 1 to 6 carbon atoms, a hydroxyalkyl group in which the alkyl group preferably contains 1 to 5 carbon atoms, or a lower (C1-C4) amidoalkyl group, or $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are in particular described in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium salt (for example chloride) homopolymers sold especially under the name Merquat 100 by the company Nalco (and its homologues of low weight-average molar mass), the product sold under the name Alcofix 131 by the company BASF, of INCI name Polyquaternium-6.

(3) quaternary copolymers of vinyllactam (vinylpyrrolidone and/or vinylcaprolactam) and of vinylimidazole.

(4) the quaternary diammonium polymers containing repeating units corresponding to formula (VII):

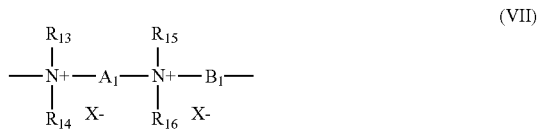

in which formula (VII):

$R_{13}$, $R_{14}$, $R_{15}$ and $R_{16}$, which may be identical or different, represent aliphatic, alicyclic or arylaliphatic radicals containing from 1 to 20 carbon atoms, or C1-C6 lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second heteroatom other than the nitrogen, or else $R_{13}$, $R_{14}$, $R_{15}$ and $R_{16}$ represent a linear or branched $C_1$-$C_6$ alkyl radical which is substituted with a nitrile, ester, acyl, amide or —CO—O—$R_{17}$-D or —CO—NH—$R_{17}$-D group in which $R_{17}$ is an alkylene and D is a quaternary ammonium group;

$A_1$ and $B_1$ represent polymethylene groups containing from 2 to 20 carbon atoms, which groups may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{13}$ and $R_{15}$ may form, with the two nitrogen atoms to which they are attached, a piperazine ring; in addition, if $A_1$ denotes a saturated or unsaturated, linear or branched alkylene or hydroxyalkylene radical, $B_1$ may also denote a group $(CH_2)_n$—CO-D-OC—$(CH_2)_p$— in which:

n and p, which may be identical or different, are integers ranging from 2 to 20 approximately, D denotes:

a) a glycol residue of formula: —O-Z-O—, where Z denotes a linear or branched hydrocarbon-based radical or a group corresponding to one of the following formulae:

—$(CH_2$—$CH_2$—$O)_x$—$CH_2$—$CH_2$—

—$[CH_2$—$CH(CH_3)$—$O]_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or alternatively the divalent radical

—$CH_2$—$CH_2$—S—S—$CH_2$—$CH_2$—;

d) a ureylene group of formula: —NH—CO—NH—.

Preferably, $X^-$ is an anion such as chloride or bromide.

These polymers have a number-average molecular mass generally between 1000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271, 378, 3,874,870, 4,001,432, 3,929,990, 3,966,904, 4,005,193, 4,025,617, 4,025,627, 4,025,653, 4,026,945 and 4,027,020.

Use may be made more particularly of polymers that are essentially formed from repeating units corresponding to the formula:

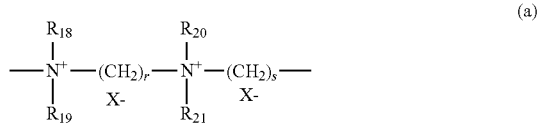

(a)

in which $R_{18}$, $R_{19}$, $R_{20}$ and $R_{21}$, which may be identical or different, denote an alkyl or hydroxyalkyl radical containing from 1 to 4 carbon atoms approximately, r and s are integers ranging from 2 to 20 approximately, and X— is an anion derived from a mineral or organic acid.

A compound of formula (a) that is particularly preferred is the one for which $R_{18}$, $R_{19}$, $R_{20}$ and $R_{21}$ represent a methyl radical and r=3, s=6 and X=Cl, which is known as Hexadimethrine chloride according to the INCI (CTFA) nomenclature.

(5) polyquaternary ammonium polymers formed from units of formula (VIII):

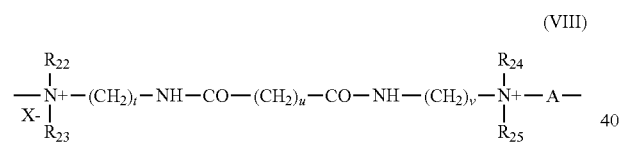

(VIII)

in which formula (VIII):

$R_{22}$, $R_{23}$, $R_{24}$ and $R_{25}$, which may be identical or different, represent a hydrogen atom or a methyl, ethyl, propyl, β-hydroxyethyl, β-hydroxypropyl or —$CH_2CH_2$(OCH$_2$CH$_2$)$_p$OH radical, in which p is equal to 0 or to an integer between 1 and 6, with the proviso that $R_{22}$, $R_{23}$, $R_{24}$ and $R_{25}$ do not simultaneously represent a hydrogen atom, t and u, which may be identical or different, are integers between 1 and 6, v is equal to 0 or to an integer between 1 and 34, X⁻ denotes an anion such as a halide, A denotes a radical of a dihalide or represents preferably —$CH_2$—$CH_2$—O—$CH_2$—$CH_2$—.

Such compounds are described especially in patent application EP-A-122 324.

Examples that may be mentioned include the products Mirapol® A15, Mirapol® AD1, Mirapol® AZ1 and Mirapol® 175 sold by the company Miranol.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among all the cationic polymers that may be used in the context of the present invention, it is preferred to use polymers of families (2) and (4), especially cationic cyclopolymers, in particular dimethyldiallylammonium chloride homopolymers, sold under the name Merquat 100 by the company Nalco (and homologues thereof of low weight-average molar masses), polymers containing units of formula (VII) and mixtures thereof, and in particular quaternary diammonium polymers formed essentially from repeating units corresponding to formula (a), for instance the polymer known as Hexadimethrine chloride according to the INCI (CTFA) nomenclature.

Amphoteric Polymer

The amphoteric (or zwitterionic) polymers that may be used in accordance with the invention may be chosen from polymers comprising units B and C distributed statistically in the polymer chain, where B denotes a unit derived from a monomer comprising at least one basic nitrogen atom and C denotes a unit derived from an acid monomer comprising one or more carboxylic or sulfonic groups, or alternatively B and C may denote groups derived from carboxybetaine or sulfobetaine zwitterionic monomers;

B and C may also denote a cationic polymer chain comprising primary, secondary, tertiary or quaternary amine groups, in which at least one of the amine groups bears a carboxylic or sulfonic group connected via a hydrocarbon-based radical or alternatively B and C form part of a chain of a polymer comprising an α,β-dicarboxylic ethylene unit in which one of the carboxylic groups has been made to react with a polyamine comprising one or more primary or secondary amine groups.

The amphoteric polymers corresponding to the definition given above that are more particularly preferred are chosen from the following polymers:

(1) polymers comprising as monomers at least one monomer derived from a vinyl compound carrying a carboxyl group, such as, more particularly, acrylic acid, methacrylic acid, maleic acid, alpha-chloroacrylic acid, and at least one basic monomer derived from a substituted vinyl compound containing at least one basic atom, chosen especially from the following:

a) dialkylaminoalkyl methacrylates, dialkylaminoalkyl acrylates, dialkylaminoalkylmethacrylamides and dialkylaminoalkylacrylamides. Such compounds are described in patent U.S. Pat. No. 3,836,537.

b) trialkylaminoalkyl methacrylate salts and trialkylaminoalkyl acrylate salts, and salts of trialkylaminoalkylmethacrylamide and of trialkylaminoalkylacrylamide.

Mention may be made especially of the acrylic acid/acrylamidopropyltrimethylammonium chloride copolymer available from the company Stockhausen under the name Polymere W3794. Mention may also be made of the acrylic acid/acrylamidopropyltrimethylammonium chloride/acrylamide copolymers available from the company Nalco under the names Merquat 2001 and Merquat 2003.

(2) polymers comprising units derived from:

a) at least one monomer chosen from acrylamides and methacrylamides substituted on the nitrogen with an alkyl radical, b) at least one acidic comonomer containing one or more reactive carboxylic groups, and c) at least one basic comonomer such as esters bearing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are more particularly chosen from acrylic, methacrylic, crotonic, itaconic, maleic and fumaric acid and alkyl monoesters, containing 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer, such as the products sold under the name Amphomer LV by the company National Starch, are particularly used.

(3) copolymers comprising as monomers at least one monomer derived from a vinyl compound bearing a carboxylic group, such as, more particularly, acrylic acid, methacrylic acid, maleic acid, alpha-chloroacrylic acid, and at least one monomer of diallyldialkylammonium salt type, the alkyl groups containing from 1 to 6 carbon atoms. Preferably, the alkyl group is a methyl group.

Among these polymers, copolymers comprising dimethyldiallylammonium chloride and acrylic acid as monomers optionally combined with acrylamide are particularly preferred. Mention may be made in particular of the compounds sold by the company Nalco under the names Merquat 280, Merquat 295, Merquat 3330, Merquat 3331 and Merquat 3333, (4) crosslinked and alkylated polyamino amides partially or totally derived from polyamino amides of general formula:

(IX)

in which R10 represents a divalent radical derived from a saturated dicarboxylic acid, a mono- or dicarboxylic aliphatic acid containing an ethylenic double bond, an ester of a lower alkanol containing 1 to 6 carbon atoms of these acids, or a radical derived from the addition of any one of said acids to a bis(primary) or bis(secondary) amine, and Z denotes a radical derived from a bis(primary), mono- or bis(secondary) polyalkylene-polyamine and preferably represents:

a) in proportions of from 60 to 100 mol %, the radical:

(X)

where x=2 and p=2 or 3, or else x=3 and p=2, this radical being derived from diethylenetriamine, triethylenetetramine or dipropylenetriamine;

b) in proportions of from 0 to 40 mol %, the radical (X) above in which x=2 and p=1 and which is derived from ethylenediamine, or the radical derived from piperazine:

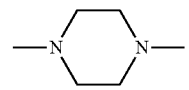

c) in proportions of 0 to 20 mol %, the radical —NH—(CH2)6-NH— derived from hexamethylenediamine, these polyaminoamines being crosslinked by addition of a difunctional crosslinking agent chosen from epihalohydrins, diepoxides, dianhydrides, bis-unsaturated derivatives, by means of 0.025 to 0.35 mol of crosslinking agent per amine group of the polyaminoamide, and being alkylated by the action of acrylic acid, chloroacetic acid or an alkane sultone or salts thereof.

The saturated carboxylic acids are preferably chosen from acids containing from 6 to 10 carbon atoms, such as adipic acid, 2,2,4-trimethyladipic acid and 2,4,4-trimethyladipic acid, terephthalic acid, acids containing an ethylenic double bond, for instance acrylic acid, methacrylic acid and itaconic acid.

The alkane sultones used in the alkylation are preferably propane sultone or butane sultone; the salts of the alkylating agents are preferably the sodium or potassium salts, (5) polymers comprising zwitterionic units of formula:

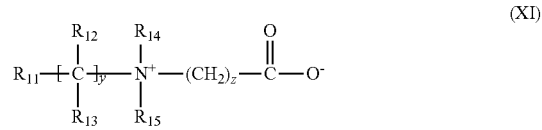

(XI)

in which R11 denotes a polymerizable unsaturated group, such as an acrylate, methacrylate, acrylamide or methacrylamide group, y and z represent an integer from 1 to 3, R12 and R13 represent a hydrogen atom, methyl, ethyl or propyl, and R14 and R15 represent a hydrogen atom or an alkyl radical such that the sum of the carbon atoms in R14 and R15 does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

Mention may be made, by way of example, of methyl methacrylate/methyl dimethylcarboxymethylammonioethyl methacrylate copolymer, such as the product sold under the name Diaformer Z301 by the company Sandoz.

(6) polymers derived from chitosan comprising monomer units corresponding to the following formulae:

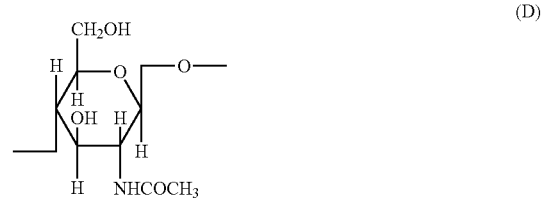

(D)

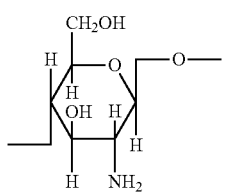
(E)

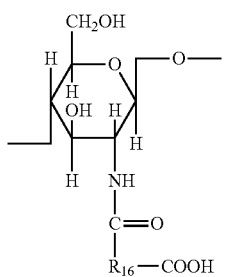
(F)

unit D being present in proportions of between 0 and 30%, unit E in proportions of between 5% and 50% and unit F in proportions of between 30% and 90%, it being understood that, in this unit F, R16 represents a radical of formula:

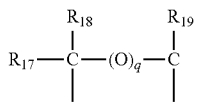

in which, if q=0, R17, R18 and R19, which may be identical or different, each represent a hydrogen atom, a methyl, hydroxyl, acetoxy or amino residue, a monoalkylamine residue or a dialkylamine residue that are optionally interrupted with one or more nitrogen atoms and/or optionally substituted with one or more amine, hydroxyl, carboxyl, alkylthio or sulfonic groups, an alkylthio residue in which the alkyl group bears an amino residue, at least one of the radicals R17, R18 and R19 being, in this case, a hydrogen atom;

or, if q=1, R17, R18 and R19 each represent a hydrogen atom, and also the salts formed by these compounds with bases or acids, (7) polymers derived from the N-carboxyalkylation of chitosan, such as N-carboxymethyl chitosan or N-carboxybutyl chitosan, sold under the name Evalsan powder by the company Jan Dekker, (8) polymers containing units corresponding to the general formula (XII) are described in French patent 1 400 366:

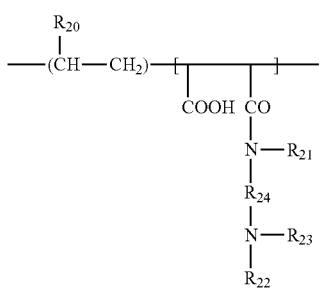
(XII)

in which R20 represents a hydrogen atom, a CH3O, CH3CH2O or phenyl radical, R21 denotes hydrogen or a lower alkyl radical such as methyl or ethyl, R22 denotes hydrogen or a lower alkyl radical such as methyl or ethyl, R23 denotes a lower alkyl radical such as methyl or ethyl or a radical corresponding to the formula: —R24-N(R22)2, R24 representing a group —CH2-CH2-, —CH2-CH2-CH2- or —CH2-CH(CH3)-, R22 having the meanings mentioned above, and also the higher homologues of these radicals and containing up to 6 carbon atoms, (9) amphoteric polymers of the -D-X-D-X— type chosen from:

a) polymers obtained by reaction of chloroacetic acid or sodium chloroacetate with compounds comprising at least one unit of formula:

-D-X-D-X-D- (XIII)

where D denotes a radical

and X denotes the symbol E or E', E or E', which may be identical or different, denote a divalent radical that is an alkylene radical with a straight or branched chain containing up to 7 carbon atoms in the main chain, which is unsubstituted or substituted with hydroxyl groups and which can comprise, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula:

-D-X-D-X— (XIV)

where D denotes a radical

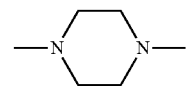

and X denotes the symbol E or E' and at least once E'; E having the meaning given above and E' is a divalent radical that is an alkylene radical bearing a straight or branched chain containing up to 7 carbon atoms in the main chain, which is unsubstituted or substituted with one or more hydroxyl radicals and comprising one or more nitrogen atoms, the nitrogen atom being substituted with an alkyl chain that is optionally interrupted with an oxygen atom and necessarily comprising one or more carboxyl functions or one or more hydroxyl functions and betainized by reaction with chloroacetic acid or sodium chloroacetate,

(10) (C1-C5)alkyl vinyl ether/maleic anhydride copolymers partially modified by semiamidation with an N,N-dialkylaminoalkylamine, such as N,N-dimethylaminopropylamine, or by semiesterification with an N,N-dialkanolamine. These copolymers may also comprise other vinyl comonomers, such as vinylcaprolactam, and mixtures thereof.

The amphoteric polymers that are particularly preferred according to the invention are those of families (1) and (3).

Mention may be made in particular of amphoteric polymers chosen from acrylic acid/acrylamidopropyltrimethylammonium chloride copolymers, acrylic acid/acrylamidopropyltrimethylammonium chloride/acrylamide copolymers, copolymers comprising dimethyldiallylammonium chloride and acrylic acid as monomers optionally combined with acrylamide, and mixtures thereof.

Compounds of family (1) will be most particularly preferred, and among these the acrylic acid/acrylamidopropyltrimethylammonium chloride copolymer.

In one variant of the invention, the cationic and/or amphoteric polymer(s) used in the composition according to the invention are in the form of powders, i.e. where appropriate in dehydrated and/or desolvated form.

In one variant, the composition according to the invention comprises at least one cationic polymer.

In another variant, the composition according to the invention comprises at least one amphoteric polymer.

d) Fatty Substances

As has already been mentioned, the composition of the invention comprises d) one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O$^-$). The fatty substances of the invention are neither polyoxyalkylenated nor polyglycerolated.

Preferably, the fatty substances used in the composition according to the invention are non-silicone oils.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, pumpkin oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in the composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this alternative form can also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose. An example that may be mentioned is the product sold under the name Glucate® DO by the company Amerchol, which is a methylglucose dioleate.

Examples of sugar esters or mixtures of sugar esters of fatty acids that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name Ryoto Sugar Esters, for example referenced B370 and corresponding to sucrose behenate formed from 20% monoester and 80% di-triester-polyester;
  the sucrose monopalmitostearate-dipalmitostearate sold by the company Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
  the Silbione® oils of the 47 and 70 047 series or the Mirasil® oils sold by Rhodia, for instance the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The organomodified silicones that may be used in accordance with the invention are silicones as defined previously and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;
oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may also be made of polyorganosiloxanes comprising:

substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
alkoxy groups such as the product sold under the name Silicone Copolymer F-755 by SWS Silicones, and Abil Wax® 2428, 2434 and 2440 by the company Goldschmidt.

Preferably, the fatty substances according to the invention are non-silicone-based.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof, which are preferably liquid.

Preferably, the fatty substance(s) are chosen from liquid petroleum jelly, polydecenes, liquid fatty alcohols, liquid esters of fatty acids and/or of fatty alcohols, or mixtures thereof.

Even more preferentially, the fatty substances are chosen from liquid petroleum jelly and octyldodecanol.

According to a particular embodiment, the composition according to the invention comprises at least 10% by weight of fatty substances, which are preferably non-silicone-based, in particular non-silicone oils, relative to the total weight of the composition. More particularly, the composition according to the invention comprises at least 25% by weight of fatty substances, which are preferably non-silicone-based, in particular non-silicone oils, relative to the total weight of the composition.

The composition according to the invention more particularly has a fatty substance content ranging from 15% to 80% by weight, preferably from 25% to 75% by weight, better still from 30% to 70% by weight and even more advantageously from 30% to 60% by weight relative to the weight of the composition.

According to a particular embodiment, when the composition contains the oxidizing agent and the basifying agent, then the composition according to the invention preferably contains at least 25% by weight of fatty substances. According to this variant, the composition preferably contains at least 30% by weight of fatty substances.

e) Basifying Agents

The composition of the invention may also comprise one or more basifying agents. The basifying agent(s) may be mineral or organic or hybrid.

The mineral basifying agent(s) are preferably chosen from ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it concerns the $pK_b$ corresponding to the functional group having the highest basicity. In addition, the organic amines do not comprise any alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (II) below:

(II)

in which formula (II) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (II) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

Preferably, the basifying agent(s) present in the composition of the invention are chosen from alkanolamines and amino acids in neutral or ionic form, in particular basic amino acids. According to a particularly preferred mode, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first embodiment, the composition predominantly contains ammonia as basifying agent.

According to another embodiment, the composition contains ammonia and at least one other basifying agent, preferably chosen from alkanolamines. In this case, the composition comprises ammonia or a salt thereof, in an amount less than the amount of basifying agent(s) other than ammonia (expressed as $NH_3$). In particular, the composition contains little or no ammonia. Preferably, according to this embodiment, the ammonia content is less than or equal to 0.03% by weight (expressed as $NH_3$), preferably less than or equal to 0.01% by weight, relative to the weight of the composition of the invention. Preferably, the composition contains no ammonia.

f) Chemical Oxidizing Agent

The composition of the invention comprises one or more chemical oxidizing agents. The term "chemical oxidizing agent" means an oxidizing agent other than atmospheric oxygen. More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates.

Advantageously, this oxidizing agent is hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Ingredients

The composition for dyeing keratin fibres according to the invention may also contain one or more surfactants chosen from nonionic surfactants such as alkylpolyglycosides, sorbitan esters, oxyethylenated fatty alcohols, and anionic, cationic or amphoteric surfactants. According to a particular embodiment, the composition contains at least one nonionic surfactant.

The composition according to the invention may also contain various ingredients conventionally used in hair dye compositions, such as anionic or nonionic polymers or mixtures thereof; mineral thickeners, and in particular fillers such as clays or talc; organic thickeners other than the cationic and/or amphoteric polymers according to the invention; antioxidants; penetrants; sequestrants; fragrances; dispersants; film-forming agents; ceramides; preserving agents; opacifiers.

The above ingredients are generally present in an amount, for each of them, of between 0.01% and 20% by weight, relative to the weight of the composition.

The composition of the invention may be in various forms, for instance a solution, an emulsion (milk or cream) or a gel, preferably in the form of an emulsion.

Processes of the Invention

The composition according to the invention is applied to wet or dry keratin fibres. It is left in place on the fibres for a time generally of from 1 minute to 1 hour and preferably from 5 minutes to 30 minutes. According to a preferred embodiment, the composition applied contains at least one basifying agent and at least one oxidizing agent.

The temperature during the dyeing process is conventionally between room temperature (between 15° C. and 25° C.) and 80° C. and preferably between room temperature and 60° C.

After the treatment, the human keratin fibres are optionally rinsed with water, optionally washed with a shampoo and then rinsed with water, before being dried or left to dry.

According to a preferred embodiment, the composition according to the invention is prepared by mixing at least two compositions, a first composition (A) which comprises the oxidation base 3-(2,5-diaminophenyl)-1-propanol and/or acid salts thereof or solvates thereof, and a second composition (B) which comprises at least one chemical oxidizing agent, it being understood that:
at least one of the compositions (A) or (B) comprises the polymer chosen from cationic polymers, amphoteric polymers and mixtures thereof, and the fatty substance(s), as defined previously, such that the fatty substance content of the composition resulting from the mixing of compositions (A)+(B) is at least 10%, preferably greater than 25%, preferably greater than 30% by weight, relative to the weight of the composition derived from the mixing of (A)+(B).

According to one embodiment, at least one of the compositions (A) or (B) is aqueous, and preferentially both compositions (A) and (B) are aqueous.

The term "aqueous composition" means a composition comprising at least 5% water. Preferably, an aqueous composition comprises more than 10% by weight of water and even more advantageously more than 20% by weight of water.

In one variant of the invention, at least part of the fatty substance(s) is present in a third composition which is mixed with compositions (A) and (B) under the conditions defined above. Preferably, this third composition is anhydrous.

More particularly, for the purposes of the invention, the term "anhydrous cosmetic composition" means a cosmetic composition with a water content of less than 5% by weight, preferably less than 2% by weight and even more preferably less than 1% by weight relative to the weight of said composition. It should be noted that the water present in the composition is more particularly "bound water", such as water of crystallization in salts, or traces of water absorbed by the starting materials used in the preparation of the compositions according to the invention.

According to a particular embodiment, the cationic and/or amphoteric polymer(s) are present in the oxidizing composition.

The examples that follow serve to illustrate the invention without, however, being limiting in nature.

EXAMPLE

Example 1

The following compositions have been prepared in which the amounts are expressed in grams of active materials.

Dye Compositions (g %)

| Chemical name | A | B |
|---|---|---|
| Sodium metabisulfite | 0.45 | 0.45 |
| Monoethanolamine | 5.83 | 5 |
| Ethylenediaminetetraacetic acid | 0.2 | 0.2 |
| 1-Methyl-2-hydroxy-4-β-hydroxyethylaminobenzene | | 0.22 |
| 1-β-Hydroxyethyloxy-2,4-diaminobenzene dihydrochloride | 0.031 | |
| 2-Methyl-1,3-dihydroxybenzene (2-methylresorcinol) | | 0.3 |
| 1-3-Dihydroxybenzene (resorcinol) | 0.96 | |
| 1-Hydroxy-3-aminobenzene | 0.15 | |
| Purified 5-amino-6-chloro-o-cresol | | 0.25 |
| 2,3-Diamino-6,7-dihydro-1H,5H-pyrazolo[1,2-a]pyrazol-1-one dimethanesulfonate | | 1.2 |
| 2-[(3-Aminopyrazolo[1,5-a]pyridin-2-yl)oxy]ethanol hydrochloride | | 0.13 |
| 3-(2,5-Diaminophenyl)propan-1-ol hydrochloride | 2.5 | 0.2 |
| Mineral oil (petroleum jelly)° | 60 | 60 |
| Polyquaternium-67 (Softcat Polymer SL-100 from Amerchol) | 0.19 | 0.19 |
| Deionized water | 17.069 | 19.47 |
| Oxyethylenated stearyl alcohol (2 OE) | 1.13 | 1.13 |
| Oxyethylenated stearyl alcohol (20 OE) | 3.88 | 3.88 |
| (50/50 $C_8/C_{10}$) Alkyl (2)-polyglucoside as a 60% aqueous solution (Oramix CG 110 from SEPPIC) | 2.4 | 2.4 |
| Oxyethylenated sorbitan monolaurate (4 OE) | 2.4 | 2.4 |
| Vitamin C | 0.25 | 0.25 |

Oxidizing Composition C (g %)

| | C |
|---|---|
| Pentasodium pentetate | 0.06 |
| Hydrogen peroxide | 6 |
| Sodium stannate | 0.04 |
| Phosphoric acid | qs pH = 2.2 |
| Tetrasodium pyrophosphate | 0.03 |
| Mineral oil (petroleum jelly) | 20 |
| Hexadimethrine chloride (Mexomere PO from Chimex) | 0.15 |
| Polyquaternium-6 (Merquat-100 from Nalco) | 0.2 |
| Water | qs 100 |
| Glycerol | 0.5 |
| Cetearyl alcohol | 6 |
| Steareth-20 | 5 |
| PEG-4 Rapeseedamide | 1.2 |
| Tocopherol | 0.1 |

At the time of use, each of the compositions A and B is mixed with one time its own weight of oxidizing composition C.

The mixtures thus obtained are applied to natural hair containing 90% white hairs.

After a leave-on time of 35 minutes at room temperature, the hair is rinsed and washed with a standard shampoo.

After drying, a beautiful light-chestnut shade is obtained on the hair with formula A and a natural coppery-red dark blond shade is obtained with formula B.

Example 2

The following compositions have been prepared in which the amounts are expressed in grams of active materials.

| | B' invention | B" comparative |
|---|---|---|
| Sodium metabisulfite | 0.45 | 0.45 |
| Monoethanolamine | 4 | 4 |
| Ethylenediaminetetraacetic acid | 0.2 | 0.2 |
| 6-HYDROXY BENZOMORPHOLINE | 0.04 | 0.04 |
| 1-BETA-HYDROXYETHYLOXY-2,4-DIAMINOBENZENE 2 Hcl | 0.16 | 0.16 |
| 2-METHYL-1,3-DIHYDROXYBENZENE (2-METHYL RESORCINOL) | 0.17 | 0.17 |
| Para aminophenol | 0.13 | 0.13 |
| 1,3-DIHYDROXYBENZENE (RESORCINOL) | 0.21 | 0.21 |
| 1-HYDROXY-3-AMINO-BENZENE | 0.16 | 0.16 |
| 3-(2,5-DIAMINOPHENYL)PROPAN-1-OL HCl | $4.18 \times 10^{-3}$ mol | — |
| 2-2 hydroxyethyl para phenylenediamine | — | $4.18 \times 10^{-3}$ mol |
| MINERAL OIL | 60 | 60 |
| PERFUME | 0.72 | 0.72 |
| Cationic Hydroxyethylcellulose (Polyquaternium-67) SOFTCAT SL-100 | 0.19 am* | 0.19 am |
| WATER | qs | qs |
| Oxyethylenated stearyl alcohol (2 OE) | 1.13 | 1.13 |
| Oxyethylenated stearyl alcohol (20 OE) | 3.88 | 3.88 |
| (50/50 $C_8/C_{10}$) Alkyl (2)-polyglucoside as a 60% aqueous solution (Oramix CG 110 from SEPPIC) | 2.4 am | 2.4 am |
| Oxyethylenated sorbitan monolaurate (4 OE) | 2.4 | 2.4 |
| Vitamin C | 0.25 | 0.25 |

*Active material

At the time of use, each composition B' and B" is mixed with the oxidizing composition C of example 1 at a weight ratio of 1/1.

The resulting mixture are each applied on natural hair locks (BN), which represents the hair root, and permed hair locks (BP), which represents the hair tips, in an amount of 10 g of composition per 1 g of hair, and left for 35 minutes at room temperature (25° C.).

Then the hair was rinsed with water, washed with the "Pro Classics concentrated" shampoo (L'Oréal Professionnel), diluted at 10%, and dried.

Selectivity Evaluation

The color of the hair was determined using the CIE L*a*b* system with a Minolta CM2006D spectrophotometer (illuminant D65, angle 10°, specular component included) in the CIELab system.

According to this system, L* indicates the lightness of the color of the hair.

The chromaticity coordinates are expressed by the parameters a* and b*, a* indicating the axis of red/green shades and b* the axis of yellow/blue shades.

The selectivity of the dyeing is measured by calculating the variation of ΔE according to the formula:

$$\Delta E = \sqrt{(L^* - L_0^*)^2 + (a^* - a_0^*)^2 + (b^* - b_0^*)^2}$$

In which L, a* and b* represent the values measured on medium sensibilized hair and L0*, a0* and b0* represent the values measured on highly sensibilized hair.

The selectivity is represented by the difference of color between the colored natural hair and sensibilized hair: the more is the ΔE value, the more the difference of color between natural and sensibized hair is important, which is representative of the homogeneity of the coloration between the raw and the tips along the lock of hair.

The following results are obtained:

|  | Hair type | L* | a* | b* | ΔE |
|---|---|---|---|---|---|
| B' + C | BN | 22.14 | 1.16 | 0.36 | 3.85 |
| (invention) | BP | 18.39 | 0.54 | −0.24 | |
| B" + C | BN | 26.24 | 2.18 | 2.04 | 5.94 |
| (comparative) | BP | 20.64 | 1.28 | 0.28 | |

The mixtures B'+C according to the invention provide less selective colorations (lower ΔE value) than the mixture of compositions B"+C (comparative): the difference between the raw and the tips is lower with B'+C than with B"+C: the coloration along the lock of hair is more homogenous with B'+C.

Example 3

The following compositions have been prepared in which the amounts are expressed in grams of active materials.

|  | D (inv) | D' (comp) |
|---|---|---|
| Ethanolamine | 4 | 4 |
| SODIUM LAURYL ETHER SULFATE (2.2 OE) 28% in aqueous solution | 2.5 | 2.5 |
| HYDROXYETHYL CELLULOSE (PM: 1.300.000) | 2.5 | 2.5 |
| Vitamine C | 0.5 | 0.5 |
| 1-METHYL-2-HYDROXY-4-BETA-HYDROXYETHYL-AMINOBENZENE | 0.5 | 0.5 |
| 1-METHYL-2-HYDROXY-4-AMINO-BENZENE | 0.5 | 0.5 |
| 1,3-DIHYDROXYBENZENE (RESORCINOL) | 0.2 | 0.2 |
| 2,3-DIAMINO-6,7-DIHYDRO-1H,5H-PYRAZOLO[1,2-A]PYRAZOL-1-ONE DIMETHANESULFONATE | $4.04 \cdot 10^{-3}$ mol | $4.04 \cdot 10^{-3}$ mol |
| 3-(2,5-DIAMINOPHE-NYL)PROPAN-1-OL-HYDROCHLORIDE | $3.43 \times 10^{-3}$ mol | — |
| 2-2 hydroxyethyl para phenylenediamine | — | $3.43 \times 10^{-3}$ mol |
| SEQUESTRANT | 2 | 2 |
| Coco-betaine | 3 am | 3 am |
| REDUCING AGENT | 0.5 | 0.5 |
| Oxyethylenated stearyl alcohol (2 OE) | 0.1 | 0.1 |
| Oxyethylenated stearyl alcohol (20 OE) | 0.1 | 0.1 |
| Mineral oil | 60 | 60 |
| PEG-40 hydrogenated castor oil | 1 | 1 |
| Water | Qsp 100 | Qsp 100 |

Oxidizing Composition E (g %)

|  | E |
|---|---|
| Hydrogen peroxide | 6 |
| Etidronic acid teratrasodic salt in aqueous solution (30%) | 0.2 |
| Tetrasodium pyrophosphate | 0.04 |
| Sodium salicylate | 0.035 |

|  | E |
|---|---|
| DIMETHYL DIALLYL AMMONIUM CHLORIDE/ACRYLIC ACID COPOLYMER (80/20) as a 60% aqueous solution in water (Merquat 280) | 0.74 |
| Caprylyl/capryl polyglucoside as a 60% aqueous solution | 3 |
| Water | qs 100 |
| Glycerol | 4 |

At the time of use, each composition D and D' is mixed with the oxidizing composition E of example 1 at a weight ratio of 1/1.

The resulting mixture are each applied on natural hair locks (BN), which represents the hair root, and permed hair locks (BP), which represents the hair tips, in an amount of 10 g of composition per 1 g of hair, and left for 35 minutes at room temperature (25° C.).

Then the hair was rinsed with water, washed with the "Pro Classics concentrated" shampoo (L'Oréal Professionnel), diluted at 10%, and dried.

The selectivity is evaluated according to the protocole of example 2.

The following results are obtained:

|  | Hair type | L* | a* | b* | ΔE |
|---|---|---|---|---|---|
| D + E | BN | 26.87 | 15.16 | 10.56 | 9.32 |
| (inv) | BP | 20.95 | 10.57 | 5.02 | |
| D' + E | BN | 29.58 | 18.40 | 13.71 | 12 |
| (comp) | BP | 21.81 | 12.78 | 6.49 | |

The mixtures D+E according to the invention provide less selective colorations (lower ΔE value) than the mixture of compositions D'+E (comparative): the difference between the raw and the tips is lower with D+E than with D'+E: the coloration along the lock of hair is more homogenous with D+E.

The invention claimed is:

1. A composition comprising:
   a) at least one oxidation base chosen from 3-(2,5-diaminophenyl)-1-propanol, acid salts thereof, solvates thereof, or hydrates thereof;
   b) at least one coupler chosen from meta-phenylenediamines, meta-aminophenols, meta-diphenols, naphthalene-based couplers, heterocyclic couplers, or the addition salts thereof;
   c) at least one polymer chosen from cationic polymers, amphoteric polymers, or mixtures thereof;
   d) at least one fatty substance, wherein the total amount of fatty substance is at least 10% by weight, relative to the total weight of the composition;
   e) optionally at least one basifying agent; and
   f) optionally at least one chemical oxidizing agent.

2. The composition of claim 1, wherein the at least one oxidation base is present in an amount ranging from about 0.0001% to about 20% by weight, relative to the total weight of the composition.

3. The composition of claim 1, wherein the cationic polymers are chosen from the following families:
   (1) homopolymers or copolymers derived from acrylic or methacrylic esters or amides and comprising at least one unit of formulae (I) to (III) below:

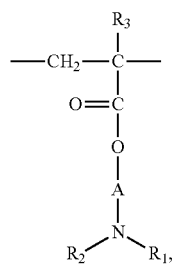
(I)

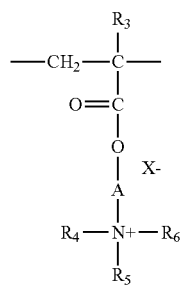
(II)

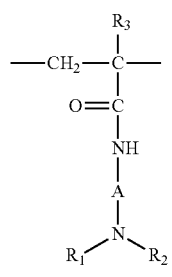
(III)

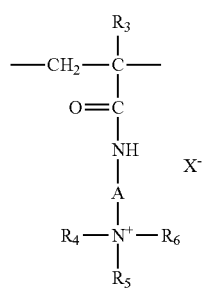
(IV)

wherein:
- $R_3$, which may be identical or different, is chosen from a hydrogen atom or a $CH_3$ radical;
- A, which may be identical or different, are chosen from a linear or branched alkyl group of 1 to 6 carbon atoms or a hydroxyalkyl group of 1 to 4 carbon atoms;
- $R_4$, $R_5$, and $R_6$, which may be identical or different, are chosen from an alkyl group containing from 1 to 18 carbon atoms or a benzyl radical;
- $R_1$ and $R_2$, which may be identical or different, are chosen from a hydrogen atom or an alkyl group containing from 1 to 6 carbon atoms;
- $X^-$ is an anion derived from a mineral or organic acid, (2) cyclopolymers of alkyldiallylamine or of dialkyldiallylammonium comprising at least one unit corresponding to formula (V) or (VI) below:

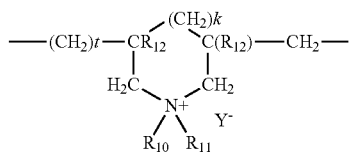
(V)

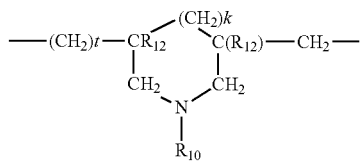
(VI)

wherein:
- k and t are equal to 0 or 1, the sum k+t being equal to 1;
- $R_{12}$ is chosen from a hydrogen atom or a methyl radical;
- $R_{10}$ and $R_{11}$, independently of each other, are chosen from an alkyl group containing from 1 to 6 carbon atoms, a hydroxyalkyl group, or a lower ($C_1$-$C_4$) amidoalkyl group, or $R_{10}$ and $R_{11}$ may represent, together with the nitrogen atom to which they are attached, heterocyclic groups;
- $Y^-$ is an anion; and
- $R_{10}$ and $R_{11}$, independently of each other, are an alkyl group containing from 1 to 4 carbon atoms, (3) quaternary polymers of vinylpyrrolidone and of vinylimidazole, (4) quaternary diammonium polymers containing repeating units corresponding to formula (VII) below:

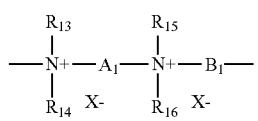
(VII)

wherein:
- $R_{13}$, $R_{14}$, $R_{15}$, and $R_{16}$, which may be identical or different, are chosen from aliphatic, alicyclic, or arylaliphatic radicals containing from 1 to 20 carbon atoms, or C1-C6 lower hydroxyalkyl aliphatic radicals, or $R_{13}$, $R_{14}$, $R_{15}$, and $R_{16}$, together or separately, constitute, with the nitrogen atoms to which they are attached, heterocycles optionally comprising a second heteroatom other than the nitrogen, or $R_{13}$, $R_{14}$, $R_{15}$, and $R_{16}$ represent a linear or branched $C_1$-$C_6$ alkyl radical which is substituted with a nitrile, ester, acyl, amide, or —CO—O—$R_{17}$-D or —CO—NH—$R_{17}$-D group wherein $R_{17}$ is an alkylene and D is a quaternary ammonium group;
- $A_1$ and $B_1$ are chosen from polymethylene groups containing from 2 to 20 carbon atoms, which may be linear or branched, saturated or unsaturated, and which may contain, linked to or intercalated in the main chain, at least one aromatic ring or at least one oxygen or sulfur atom or sulfoxide, sulfone, disulfide, amino, alkylamino, hydroxyl, quaternary ammonium, ureido, amide, or ester groups;
- $X^-$ is an anion derived from a mineral or organic acid;
- $A_1$ $R_{13}$, and $R_{15}$ may form, with the two nitrogen atoms to which they are attached, a piperazine ring;
- wherein, if $A_1$ represents a saturated or unsaturated, linear or branched alkylene or hydroxyalkylene radical, $B_1$ may also represent a (CH2)n-CO-D-OC—(CH2)p- group
wherein:
n and p, which may be identical or different, are integers ranging from 2 to 20,
D is chosen from:
a) a glycol residue of formula: —O—Z—O—, wherein Z is a linear or branched hydrocarbon-based radical or a group corresponding to one of the following formulae:

—(CH$_2$—CH$_2$—O)$_x$—CH$_2$—CH$_2$—

—[CH$_2$—CH(CH$_3$)—O]$_y$—CH$_2$—CH(CH$_3$)— wherein x and y are an integer ranging from 1 to 4, representing a defined and unique degree of polymerization or any number from 1 to 4 representing an average degree of polymerization;
b) a bis-secondary diamine residue;
c) a bis-primary diamine residue of formula: —NH—Y—NH—, wherein Y is a linear or branched hydrocarbon-based radical, or alternatively the divalent radical—CH$_2$—CH$_2$—S—S—CH$_2$—CH$_2$—; or
d) a ureylene group of formula: —NH—CO—NH—,
(5) polyquaternary ammonium polymers formed from units of formula (VIII):

$$-\underset{\underset{R_{23}}{|}}{\overset{\overset{R_{22}}{|}}{N^+}}-(CH_2)_t-NH-CO-(CH_2)_u-CO-NH-(CH_2)_v-\underset{\underset{R_{25}}{|}}{\overset{\overset{R_{24}}{|}}{N^+}}-A- \quad \text{(VIII)}$$
$X^-$ wherein:
$R_{22}$, $R_{23}$, $R_{24}$, and $R_{25}$, which may be identical or different, are chosen from a hydrogen atom or a methyl, ethyl, propyl, β-hydroxyethyl, β-hydroxypropyl, or —CH2CH2(OCH2CH2)pOH radical wherein p is equal to 0 or an integer between 1 and 6, wherein $R_{22}$, $R_{23}$, $R_{24}$, and $R_{25}$ do not simultaneously represent a hydrogen atom;
t and u, which may be identical or different, are chosen from integers between 1 and 6;
v is equal to 0 or an integer between 1 and 34;
$X^-$ is an anion; and
A is a radical of a dihalide,
(6) polyalkyleneimines, polymers comprising vinylpyridine or vinylpyridinium units, condensates of polyamines and of epichlorohydrin, quaternary polyureylenes, or chitin derivatives,
or mixtures thereof.

4. The composition of claim 3, wherein the cationic polymers are chosen from families (2) and (4).

5. The composition of claim 3, wherein the cationic polymers are chosen from cationic cyclopolymers, polymers containing units of formula (VII), or mixtures thereof.

6. The composition of claim 1, wherein the amphoteric polymers are chosen from the following compounds:
(1) polymers comprising as monomers at least one monomer derived from a vinyl compound carrying a carboxyl group, and at least one basic monomer derived from a substituted vinyl compound containing at least one basic atom, chosen from the following:

a) dialkylaminoalkyl methacrylates, dialkylaminoalkyl acrylates, dialkylaminoalkylmethacrylamides, or dialkylam inoalkylacrylam ides; or
b) trialkylaminoalkyl methacrylate salts, trialkylaminoalkyl acrylate salts, or salts of trialkylaminoalkylmethacrylamide and of trialkylaminoalkylacrylamide;
(2) polymers comprising units derived from:
a) at least one monomer chosen from acrylamides and methacrylamides substituted on the nitrogen with an alkyl radical,
b) at least one acidic comonomer containing at least one reactive carboxylic group, and
c) at least one basic comonomer;
(3) copolymers comprising as monomers at least one monomer derived from a vinyl compound bearing a carboxylic group, and at least one monomer of diallyldialkylammonium salt type, the alkyl groups containing from 1 to 6 carbon atoms;
(4) crosslinked and alkylated polyamino amides partially or totally derived from polyamino amides of general formula:

$$-[CO-R_{10}-CO-Z]- \quad \text{(IX)}$$

wherein $R_{10}$ is chosen from a divalent radical derived from a saturated dicarboxylic acid, a mono- or dicarboxylic aliphatic acid containing an ethylenic double bond, an ester of a lower alkanol containing 1 to 6 carbon atoms of these acids, or a radical derived from the addition of any one of said acids to a bis(primary) or bis(secondary) amine, and Z is a radical derived from a bis(primary), mono- or bis(secondary) polyalkylene-polyamine and represents:
a) in proportions of from 60 to 100 mol %, the radical:

$$-\underset{H}{N}-[(CH_2)_x-\underset{H}{N}]_p- \quad \text{(X)}$$

wherein x is equal to 2 and p is equal to 2 or 3, or else x is equal to 3 and p is equal to 2, this radical being derived from diethylenetriamine, triethylenetetramine or dipropylenetriamine;
b) in proportions of from 0 to 40 mol %, the radical (X) above wherein x is equal to 2 and p is equal to 1 and which is derived from ethylenediamine, or the radical derived from piperazine:

—N⟨ ⟩N— c) in proportions of 0 to 20 mol %, the radical —NH—(CH$_2$)6-NH— derived from hexamethylenediamine, these polyaminoamines being crosslinked by addition of a difunctional crosslinking agent chosen from epihalohydrins, diepoxides, dianhydrides, bis-unsaturated derivatives, by means of 0.025 to 0.35 mol of crosslinking agent per amine group of the polyaminoamide, and being alkylated by the action of acrylic acid, chloroacetic acid, or an alkane sultone, or salts thereof;

(5) polymers comprising zwitterionic units of formula:

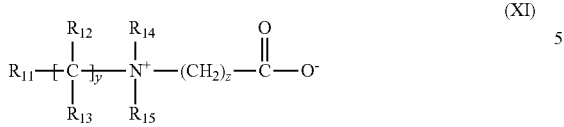

wherein:
R11 is a polymerizable unsaturated group,
y and z are an integer ranging from 1 to 3,
$R_{12}$ and $R_{13}$ are chosen from a hydrogen atom, methyl, ethyl, or propyl, and
$R_{14}$ and $R_{15}$ are chosen from a hydrogen atom or an alkyl radical wherein the sum of the carbon atoms in $R_{14}$ and $R_{15}$ does not exceed 10;
(6) polymers derived from chitosan comprising monomer units corresponding to the following formulae:

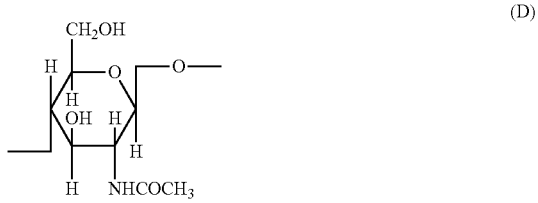

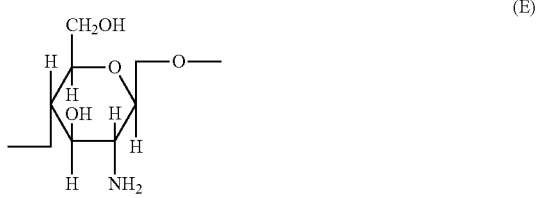

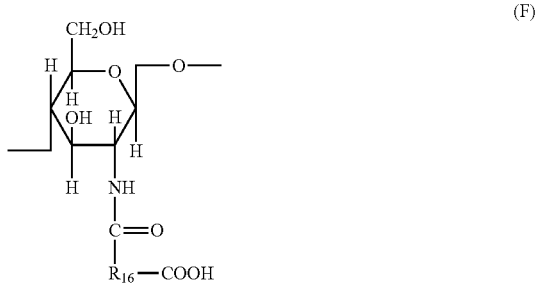

wherein unit D is present in proportions ranging from about 0% to about 30%, unit E is present in proportions ranging from about 5% to about 50%, and unit F is present in proportions ranging from about 30% to about 90%, wherein in unit F, $R_{16}$ is chosen from a radical of formula:

wherein, if q is equal to 0, $R_{17}$, $R_{18}$, and $R_{19}$, which may be identical or different, each represent a hydrogen atom, a methyl, hydroxyl, acetoxy or amino residue, a monoalkylamine residue or a dialkylamine residue that are optionally interrupted with at least one nitrogen atom or optionally substituted with at least one amine, hydroxyl, carboxyl, alkylthio or sulfonic group, an alkylthio residue wherein the alkyl group bears an amino residue, at least one of the radicals $R_{17}$, $R_{18}$, and $R_{19}$ being, in this case, a hydrogen atom;
or, if q is equal to 1, $R_{17}$, $R_{18}$, and $R_{19}$ each represent a hydrogen atom, and also the salts formed by these compounds with bases or acids;
(7) polymers derived from the N-carboxyalkylation of chitosan;
(8) polymers containing units corresponding to the general formula (XII):

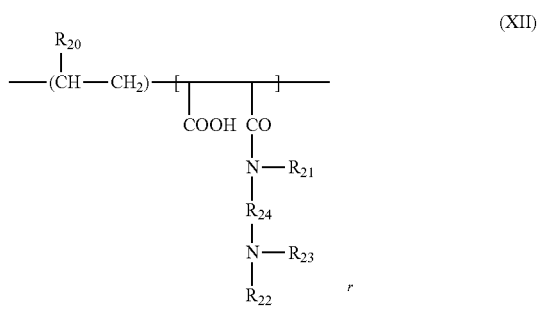

wherein:
$R_{20}$ is chosen from a hydrogen atom, a CH3O, CH3CH2O, or phenyl group,
$R_{21}$ is chosen from a hydrogen atom or a lower alkyl radical,
$R_{22}$ is chosen from a hydrogen atom or a lower alkyl radical,
$R_{23}$ is chosen from a lower alkyl radical or a radical corresponding to the formula: —R24-N(R22)2, wherein R24 is chosen from a —CH2—CH2—, —CH2—CH2—CH2— or —CH2—CH(CH3)- group, and is chosen from a hydrogen atom or a lower alkyl radical,
and wherein the higher homologues of these radicals contain up to 6 carbon atoms;
(9) amphoteric polymers of the -D-X-D-X— type chosen from:
a) polymers obtained by reaction of chloroacetic acid or sodium chloroacetate with compounds comprising at least one unit of formula:

-D-X-D-X-D- (XIII)

wherein D is a radical

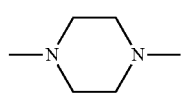

and X represents the symbol E or E', which may be identical or different, chosen from a divalent radical that is an alkylene radical with a straight or branched chain containing up to 7 carbon atoms in the main chain, which is unsubstituted or substituted with hydroxyl groups and which can comprise, in addition to the oxygen, nitrogen, and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups, or
b) polymers of formula:

-D-X-D-X— (XIV)

wherein D is a radical

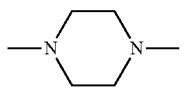

and X represents the symbol E or E', wherein at least one X represents E', wherein E is chosen from a divalent radical that is an alkylene radical with a straight or branched chain containing up to 7 carbon atoms in the main chain, which is unsubstituted or substituted with hydroxyl groups and which can comprise, in addition to the oxygen, nitrogen, and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups and E' is a divalent radical that is an alkylene radical bearing a straight or branched chain containing up to 7 carbon atoms in the main chain, which is unsubstituted or substituted with at least one hydroxyl radical and comprising at least one nitrogen atom, the nitrogen atom being substituted with an alkyl chain that is optionally interrupted with an oxygen atom and necessarily comprising at least one carboxyl function or at least one hydroxyl function and betainized by reaction with chloroacetic acid or sodium chloroacetate;

(10) (C1-C5)alkyl vinyl ether/maleic anhydride copolymers partially modified by semiamidation with an N,N-dialkylaminoalkylamine or by semiesterification with an N, N-dialkanolamine; or mixtures thereof.

7. The composition of claim 1, wherein the amphoteric polymers are chosen from acrylic acid/acrylamidopropyltrimethylammonium chloride copolymers, acrylic acid/acrylamidopropyltrimethylammonium chloride/acrylamide copolymers, copolymers comprising dimethyldiallylammonium chloride and acrylic acid as monomers optionally combined with acrylamide, or mixtures thereof.

8. The composition of claim 1, wherein the at least one polymer is present in an amount ranging from about 0.01% to about 10% by weight, relative to the total weight of the composition.

9. The composition of claim 1, wherein the at least one fatty substance is chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids, esters of fatty alcohols other than triglycerides and plant waxes, non-silicone waxes, silicones, or mixtures thereof.

10. The composition of claim 1, wherein the at least one fatty substance is chosen from $C_6$-$C_{16}$ hydrocarbons, hydrocarbons containing more than 16 carbon atoms, triglycerides, fatty alcohols, esters of fatty acids, esters of fatty alcohols other than triglycerides, or mixtures thereof.

11. The composition of claim 1, wherein the at least one fatty substance is liquid at room temperature and at atmospheric pressure.

12. The composition of claim 1, wherein the total amount of fatty substance ranges from 15% to 80% by weight, relative to the total weight of the composition.

13. The composition of claim 1, wherein the at least one basifying agent is chosen from ammonia, alkali metal carbonates or bicarbonates, sodium hydroxide or potassium hydroxide, organic amines chosen from alkanolamines, oxyethylenated, or oxypropylenated ethylenediamines, amino acids, compounds of formula (II) below, or mixtures thereof:

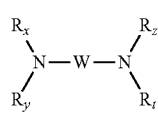

wherein:
W is a divalent $C_1$-$C_6$ alkylene radical optionally substituted with at least one hydroxyl group or a $C_1$-$C_6$ alkyl radical, and/or optionally interrupted with at least one heteroatom or $NR_u$; and
$R_x$, $R_y$, $R_z$, $R_t$, and $R_u$, which may be identical or different, are chosen from a hydrogen atom or a $C_1$-$C_6$ alkyl, $C_1$-$C_6$ hydroxyalkyl or $C_1$-$C_6$ aminoalkyl radical.

14. The composition of claim 1, wherein the at least one basifying agent is chosen from ammonia or alkanolamines, or neutral or ionic amino acids.

15. The composition of claim 1, wherein the at least one chemical oxidizing agent is hydrogen peroxide.

16. A process for dyeing keratin fibers, comprising:
applying to the keratin fibers a composition comprising:
a) at least one oxidation base chosen from 3-(2,5-diaminophenyl)-1-propanol acid salts thereof, solvates thereof, or hydrates thereof;
b) at least one coupler chosen from meta-phenylenediamines, meta-aminophenols, meta-diphenols, naphthalene-based couplers, heterocyclic couplers, or the addition salts thereof;
c) at least one polymer chosen from cationic polymers, amphoteric polymers, or mixtures thereof;
d) at least one fatty substance, wherein the total amount of fatty substance is at least 10% by weight, relative to the total weight of the composition;
e) optionally at least one basifying agent; and
f) optionally at least one chemical oxidizing agent.

17. The process of claim 16, wherein the composition is obtained by mixing at least two compositions,
a first composition (A) comprising the at least one oxidation base; and
a second composition (B) comprising the at least one chemical oxidizing agent;
wherein at least one of the compositions (A) or (B) comprises the at least one polymer; and wherein the amount of the at least one fatty substance in the composition resulting from the mixing of compositions (A) and (B) is greater than 30% by weight, relative to the weight of the composition derived from the mixing of (A) and (B).

18. The process of claim 17, wherein the composition applied to the fibers comprises a third composition comprising the at least one fatty substance.

19. A multi-compartment device comprising:
a first compartment containing composition (A) comprising at least one oxidation base chosen from 3-(2,5-diaminophenyl)-1-propanol, acid salts thereof, solvates thereof, or hydrates thereof; and
a second compartment containing composition (B) comprising at least one chemical oxidizing agent;
wherein at least one of the compositions (A) or (B) comprises at least one polymer chosen from cationic polymers, amphoteric polymers, or mixtures thereof, and at least one fatty substance;
wherein the total amount of fatty substance is present in the composition resulting from the mixing of compositions (A) and (B) in an amount of at least 10% by weight, relative to the weight of the composition derived from the mixing of (A) and (B).

* * * * *